US00PP08299P

United States Patent [19]

VandenBerg

[11] Patent Number: Plant 8,299

[45] Date of Patent: Jul. 13, 1993

[54] CHRYSANTHEMUM PLANT NAMED REGAL PASADENA

[75] Inventor: Cornelis P. VandenBerg, Salinas, Calif.

[73] Assignee: Yoder Brothers, Inc., Barberton, Ohio

[21] Appl. No.: 743,094

[22] Filed: Aug. 9, 1991

[51] Int. Cl.[5] ..... A01H 5/00

[52] U.S. Cl. ..... Plt./74.1

[58] Field of Search ..... Plt./74.1, 82.5

[56] References Cited

U.S. PATENT DOCUMENTS

P.P. 6,112 2/1988 Shoesmith ..... Plt. 74.1
P.P. 6,204 6/1988 Hesse ..... Plt. 74.1
4,616,099 10/1986 Sparkes ..... 47/58

OTHER PUBLICATIONS

Gosling, ed., 1979, "the Chrysanthemum Manual-6th Edition", the National Chrysanthemum Society, London, Essex Telegraph Press, Ltd. pp. 329-336.

Broertjes, et al., 1978, "Application of Mutation Breeding Methods in the Improvement of Vegetatively Propagated Crops", Elsevier Sci. Pub. Co., New York, pp. 162-175.

Broertjes, et al., "A Mutant of a Mutant of a . . . Irradiation of Progressive Radiation-Induced Mutants in a Mutation Breeding Programme with *C. morifolium*", Euphytica, 29:526-530.

Searle, et al., 1968, "Chrysanthemums the Year Round", Blanford Press, London, pp. 27-29, 320-327.

Chan, 1966, "Chrysanthemum and Rose Mutations Induced by X-rays", Am. Sec. Hort. Sci. Proc., pp. 613-620.

Broertjes, 1966, "Mutation Breeding of Chrysanthemums", Euphytica, 15:156-162.

Dowrick, et al., "The Induction of Mutations in Chrysanthemum using X-and Gamma Radiation", Euphytica, 15:204-210.

*Primary Examiner*—Howard J. Locker
*Attorney, Agent, or Firm*—Foley & Lardner

[57] ABSTRACT

A Chrysanthemum plant named Regal Pasadena particularly characterized by its flat capitulum form; spoon daisy capitulum type; dark red-purple ray floret color; diameter across face of capitulum of 127 to 152 mm when fully opened, when grown as a pinched disbudded pot mum; photoperiodic flowering response to short days of 46 to 48 days; plant height, with 15 to 23 long days after sticking unrooted cuttings, and with 1 application of 2500 ppm B-9 SP, ranges from 20 to 23 cm when grown as a pinched pot mum with 4 cuttings in a 15 cm pot; branching pattern is spreading and prolific, each plant having 3 to 5 laterals after pinch; and recommended as disbudded pot mum.

1 Drawing Sheet

The present invention comprises a new and distinct cultivar of Chrysanthemum, botanically known as *Dendranthema grandiflora,* and referred to by the cultivar name Regal Pasadena.

Regal Pasadena, identified as 4003 (84-Y91A02), is a product of a mutation induction program. The new cultivar was discovered and selected by Cornelis P. VandenBerg on Oct. 3, 1989 in a controlled environment in Salinas, Calif., as one flowering plant within a flowering block established as rooted cuttings from stock plants which had been exposed as unrooted cuttings to an X-ray source of 2000 rads in Fort Myers, Fla., in April 1989. The irradiated parent cultivar was the cultivar identified as Pasadena, disclosed in U.S. Plant Pat. No. 7,346, and described as a spoon daisy disbud pot mum with a flat capitulum form; dark red-purple ray floret color; diameter across face of capitulum of 127 to 159 mm when fully opened; flowering response period of 44 to 51 days after start of short days; plant height of 18 to 30 cm with 1 to 2 applications of 2500 ppm B-9 SP when grown as a pinched pot mum in a 15 cm pot; and spreading and prolific branching pattern, with 4 to 5 laterals after pinch.

The irradiation program resulting in Regal Pasadena had at its primary objective the expansion of color ranges of the parent cultivar Pasadena. The irradiation program comprised irradiating cuttings of the parent cultivar at irradiation levels of 1500, 1750 and 2000 rads. A total of 1042 cuttings harvested from a total of 225 irradiated plants were planted on Jul. 31, Jul. 24 and Jul.

10, 1989. Of these, 6 initial selections were made, which selections were then revegetated and reflowered. Three consecutive flowerings resulted in discarding 5 of the original 6 selections on Jul. 17, 1990. One selection was maintained for commercial introduction as Regal Pasadena.

The first act of asexual reproduction of Regal Pasadena was accomplished when vegetative cuttings were taken from the initial selection in December 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Regal Pasadena are firmly fixed and are retained through successive generations of asexual reproduction.

Regal Pasadena has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Regal Pasadena, which, in combination, distinguish this Chrysanthemum as a new and distinct cultivar:

1. Flat capitulum form.
2. Spoon daisy capitulum type.
3. Dark red-purple ray floret color.
4. Diameter across face of capitulum of 127 to 152 mm when fully opened, when grown as a pinched disbudded pot mum.
5. Photoperiodic flowering response to short days of 46 to 48 days.
6. Plant height, with 15 to 23 long days after sticking unrooted cuttings, and with 1 application of 2500 ppm B-9 SP, ranges from 20 to 23 when grown as a pinched pot mum with 4 cuttings in a 15 cm pot.
7. Branching pattern is spreading, each plant having 3 to 5 laterals after pinch.
8. Recommended as disbudded pot mum.

The accompanying photographic drawing is a side view of a potted mum of Regal Pasadena, with 4 cuttings in a 15 cm pot, with the colors being as nearly true as possible with illustrations of this type.

Of the commercial cultivars known to the inventor, the most similar in comparison to Regal Pasadena is the parent cultivar Pasadena. In comparison with Pasadena, Regal Pasadena has a darker ray floret color, and has significantly longer spoons and a shorter tubular base than Pasadena. In addition, it has been noted in our flowering trials that Regal Pasadena has a slightly smaller diameter of capitulum by 1 cm when compared to Pasadena, and slightly less vigor when compared side by side to Pasadena in the same flowering trial. When comparing the description of Regal Pasadena with that of Pasadena, it is evident that Pasadena has a wider range for many characteristics than Regal Pasadena. The reason for this is that the description of Pasadena is based on evaluations over a time period of more than three years, while the description of Regal Pasadena is based on considerably less flowerings in a time period of approximately seven months.

In the following description color references are made to the Royal Horticultural Society Colour chart. The color values were determined on plant material grown as a pinched disbudded pot mum in Salinas, Calif. on Mar. 22, 1991.

Classification:

*Botanical.*—*Dendranthema grandiflora* cv. Regal Pasadena.

*Commercial.*—Flat spoon daisy disbud pot mum.

INFLORESCENCE

A. Capitulum:
- *Form.*—Flat.
- *Type.*—Spoon daisy.
- *Diameter across face.*—127 to 152 mm when fully opened, when grown as a pinched disbudded pot mum.

B. Corolla of ray florets:
- *Color (general tonality from a distance of three meters).*—Dark red-purple.
- *Color of spoon tips.*—59A.
- *Color of tubes.*—186D, slightly overlaid and streaked with 59A.
- *Shape.*—Base tubular. Distal portion open, flattened and spoon-like. The length of the flattened spoon in many instances comprises up to 90% of the total petal length.

C. Corolla of disc florets:
- *Color (mature).*—7A.
- *Color (immature).*—144A to 144B.

D. Reproductive organs:
- *Androecium.*—Present on disc florets only; no pollen.
- *Gynoecium.*—Present on both ray and disc florets.

PLANT

A. General appearance:
- *Height.*—20 to 23 cm when grown as a pinched pot mum in a 15 cm pot with 15 to 23 long days after sticking unrooted cuttings and with 1 application of 2500 ppm B-9 SP.
- *Branching pattern.*—Spreading, with 3 to 5 laterals after pinch.

B. Foliage:
- *Color (upper surface).*—147A.
- *Color (under surface).*—147B.
- *Shape.*—Lobed and slightly serrated.

I claim:

1. A new and distinct Chrysanthemum plant named Regal Pasadena, as described and illustrated.

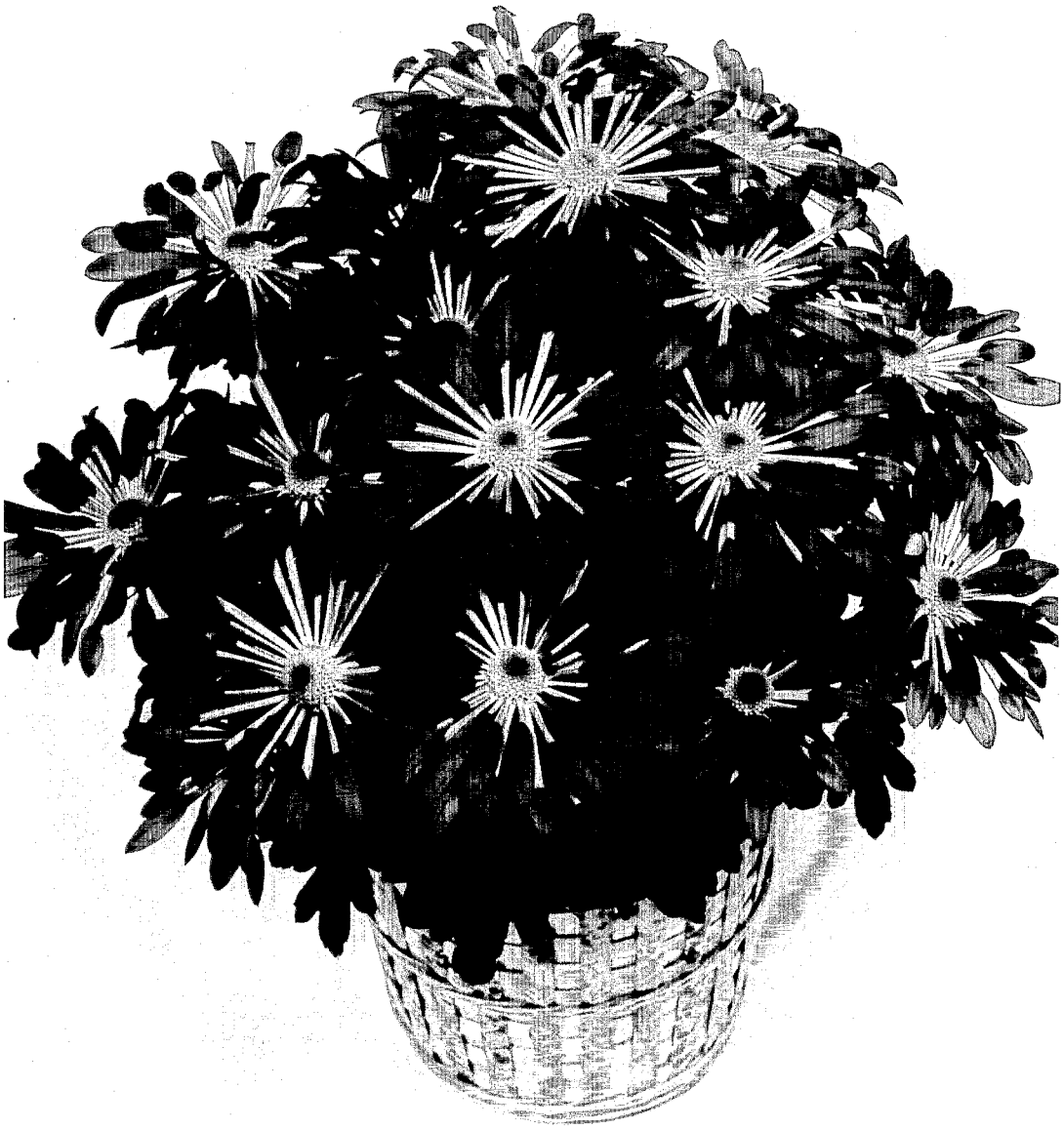

* * * * *